United States Patent [19]

Jelich

[11] Patent Number: 4,990,622
[45] Date of Patent: *Feb. 5, 1991

[54] PROCESS FOR THE PREPARATION OF 2-CHLORO-5-CHLOROMETHYLPYRIDINE

[75] Inventor: Klaus Jelich, Wuppertal, Fed. Rep. of Germany

[73] Assignee: Bayer Aktiengesellschaft, Leverkusen, Fed. Rep. of Germany

[ * ] Notice: The portion of the term of this patent subsequent to Sep. 18, 2007 has been disclaimed.

[21] Appl. No.: 447,145

[22] Filed: Dec. 6, 1989

[30] Foreign Application Priority Data

Dec. 16, 1988 [DE] Fed. Rep. of Germany ....... 3842359

[51] Int. Cl.$^5$ .......................................... C07D 213/26
[52] U.S. Cl. ..................................................... 546/345
[58] Field of Search ......................................... 546/345

[56] References Cited

FOREIGN PATENT DOCUMENTS 0009212  4/1980  European Pat. Off. .
0065358 11/1982 European Pat. Off. .
0163855 12/1985 European Pat. Off. .
0192060  8/1986  European Pat. Off. .
0254859  2/1988  European Pat. Off. .
0259738  3/1988  European Pat. Off. .

OTHER PUBLICATIONS

Dainter, Ronald S. "Abnormal Nucleophilic Substitution . . . "*Tetrahedron Letters*, vol. 25, No. 49, pp. 5693–5696, 1984.
Tilley, Jefferson, "Synthesis of Heterocyclic Analogs of α-Methyl-Dopa", *J. Heterocyclic Chem.*, 16, pp. 333–337, 1979.

Primary Examiner—Mary C. Lee
Assistant Examiner—Jacqueline Haley
Attorney, Agent, or Firm—Sprung Horn Kramer & Woods

[57] ABSTRACT

A process for the preparation of 2-chloro-5-chloromethylpyridine of the formula (I)

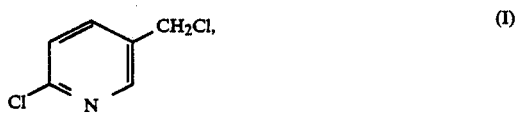

which is used as an intermediate for the preparation of insecticides, the process comprising (a) reacting in a first step nicotinic acid of the formula (II)

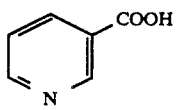

with phosphorus pentachloride, if appropriate in the presence of thionyl chloride and if appropriate in the presence of a diluent, (b) reacting in a second step the resulting 3-trichloromethylpyridine from the first step, of the formula III,

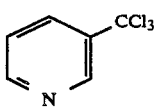

with an alkali metal alkoxide of the formual (IV)

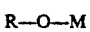

in which
R represents alkyl and
M represents an alkali metal cation,
if appropriate in the presence of a diluent, (c) reacting in a third step the resulting pyridine ether acetal from the second step, of the formula (V),

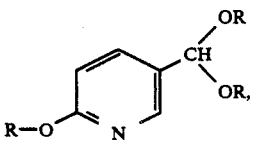

in which R has the abovementioned meaning
with water, if appropriate in the presence of a catalyst acid, (d) hydrogenating in a fourth step the resulting pyridine aldehyde from the third step, of the formula (VI),

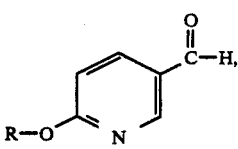

in which R has the abovementioned meaning
with molecular hydrogen in the presence of a hydrogenation catalyst and, if appropriate, in the presence of a diluent, and, finally, (e) reacting in a fifth step the resulting pyridylmethanol from the fourth step of the formula (VII),

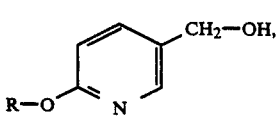

in which R has the abovementioned meaning.

13 Claims, No Drawings

PROCESS FOR THE PREPARATION OF 2-CHLORO-5-CHLOROMETHYLPYRIDINE

The invention relates to a new process for the preparation of 2-chloro-5-chloromethylpyridine, which is used as an intermediate for the preparation of known insecticides.

It is known that 2-chloro-5-chloromethylpyridine is obtained in a complicated, multi-step process when 2-chloropyridine-5-carboxylic acid is converted into the corresponding acid chloride using thionyl chloride, this acid chloride, if appropriate, is esterified with ethanol and subsequently reduced to give the hydroxymethyl compound using sodium boranate, and the hydroxyl group in the side chain is finally substituted by chlorine using thionyl chloride (cf., for example, U.S. Pat. No. 4,576,629; J. Org. Chem. 34, 3545 [1969]; J. Heterocycl. Chem. 16, 333–337 [1979]).

However, disadvantageous in this process and prohibitive for a large-scale industrial feasibility are the high costs of the starting compound 2-chloropyridine-5-carboxylic acid and of the reducing agent sodium boranate, which, additionally, is also a safety problem with regard to the evolution of hydrogen in the course of the reaction.

Furthermore, it is known that 2-chloro-5-chloromethylpyridine is obtained when 2-chloro-5-methylpyridine is reacted with elemental chlorine (cf., for example, DE-A 3,630,046). However, the disadvantage in this process is that the reaction does not proceed uniformly, which makes it necessary to disrupt the chlorination at an early point in time to avoid formation of substantial amounts of multichlorinated by-products, before the reaction could proceed to completion (cf. also EP-A 9,212; EP-A 65,358). The mixtures formed can only be separated with difficulty and yield products of a purity which is unsatisfactory.

It has now been found that 2-chloro-5-chloromethylpyridine, of the formula (I),

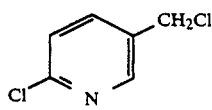

is obtained in high yield and high purity when, initially in a 1st step, nicotinic acid, of the formula (II),

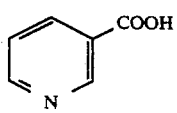

is reacted with phosphorus pentachloride, if appropriate in the presence of thionyl chloride and if appropriate in the presence of a diluent, the resulting 3-trichloromethylpyridine, of the formula

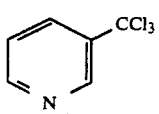

is then reacted, in a 2nd step, with alkali metal alkoxides of the formula (IV)

in which
R represents alkyl and
M represents an alkali metal cation,
if appropriate in the presence of a diluent, the resulting pyridine ether acetals of the formula (V)

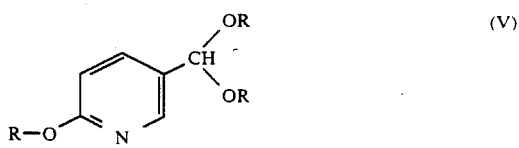

in which R has the abovementioned meaning are then reacted in a 3rd step with water, if appropriate in the presence of a catalyst acid, the resulting pyridine aldehydes of the formula (VI)

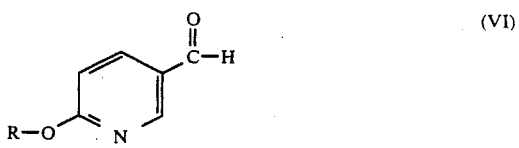

in which R has the abovementioned meaning are than hydrogenated in the 4th step with molecular hydrogen in the presence of a hydrogenation catalyst and, if appropriate, in the presence of a diluent, and, finally, the resulting pyridylmethanols of the formula (VII)

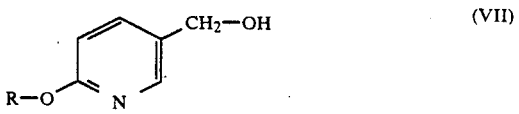

in which R has the abovementioned meaning are reacted in a 5th step with a chlorinating agent, if appropriate in the presence of a diluent and if appropriate in the presence of a reaction auxiliary, it also being possible for either step two and step three, or step three and step four, or step two, step three and step four, to be carried out directly in one reaction step without isolation of intermediates (so-called "one-pot reactions").

A series of aspects of the reaction sequence according to the invention must be classified as entirely surprising and not predictable for those skilled in the art. Furthermore, the combination of the 5 reaction steps makes the entire process novel and inventive.

Thus, for example, it could not be expected that the reaction of nicotinic acid with phosphorus pentachloride or with phosphorus pentachloride in the presence of thionyl chloride, respectively, according to step one of the process according to the invention would give the desired 3-trichloromethylpyridine of the formula (III) in a smooth reaction and in very high yields, since, on the one hand, it was known from the prior art that phenylphosphine chlorides, which are highly reactive, complicated to prepare and difficult to handle, are required as chlorinating agents or reaction auxiliaries in order to achieve a higher yield (cf., in this context, U.S. Pat. No. 4,634,771), and since, on the other hand, investigations by the applicant company had revealed that the simple, direct reaction of nicotinic acid with phosphorus pentachloride (cf., in this context, Tetrahedron Letters 25, 5693–5696 [1984]) in substance or also in the presence of diluents give yields of only a maximum of 5% of desired trichloromethylpyridine compound of the formula (III).

Another unpredictable aspect was the fact that the reaction of 2-alkoxy-5-pyridylmethanols of the formula (VII) with chlorinating agents, such as, for example, phosphorus oxychloride or phosgene, according to step five of the process according to the invention would result in a simultaneous exchange both of the hydroxyl group and of the alkoxy group for one chlorine radical each, since, on the one hand, it was known from the prior art that either "Vilsmeier-Haack conditions" (that is to say, phosphorus oxychloride in the presence of large amounts of dimethylformamide, which on working up gives considerable amounts of waste water), which are generally unsuitable for large-scale industrial operation, would be required for converting 2-methoxypyridine into 2-chloropyridine, in which process phosphorus oxychloride in the absence of dimethylformamide would not cause any type of reaction. In addition, at a yield of less than 40% this reaction yields only a highly impure product, whose purification by chromatography is complicated (cf., in this context, Synthesis 1984, 743–745). On the other hand, it was known that comparable reactions with thionyl chloride also exclusively cause an exchange on the hydroxyl group, the ether function remaining unaltered (cf., in this context, European Patent No. 163,855).

Finally, it could also not have been predicted that it would be possible to carry out either step two and step three of the process according to the invention, or step three and step four of the process according to the invention, or step two, step three and step four of the process according to the invention directly without isolation of the intermediates, since such "one-pot reactions" give satisfactory results only in exceptional cases, in particular when they cover more than two reaction steps, usually result in considerable yield losses and/or require complicated reaction operations.

A particular advantage of the reaction sequence according to the invention which must be emphasized is that the starting substance nicotinic acid is an inexpensive starting material which can be produced industrially on a large scale; furthermore that all reactions can be carried out using readily accessible reagents, under reaction conditions which are selective and readily available under industrial conditions, and in high yields, and that, last but not least, in particular the abovementioned variants without the isolation of certain intermediates result in a rational and economic synthesis of the desired target compound.

If, for example, nicotinic acid is used as the starting compound, thionyl chloride and phosphorus pentachloride as the reactants in step one, sodium methoxide as the resultant in step two, dilute hydrochloric acid as the reaction auxiliary in step three, palladium on active carbon as the hydrogenation catalyst in step four, and phosgene in the presence of dibutylformamide as the chlorinating agent in step five, the course of the reaction of the process according to the invention may be represented by the following equation:

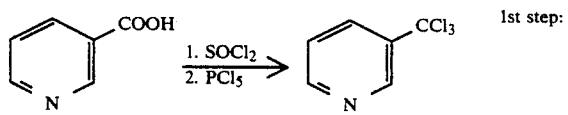

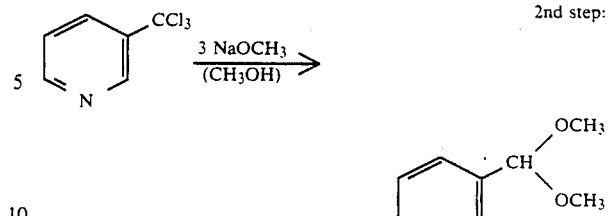

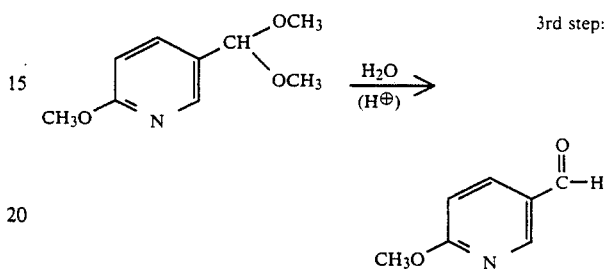

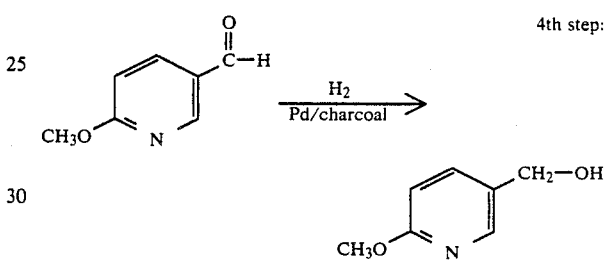

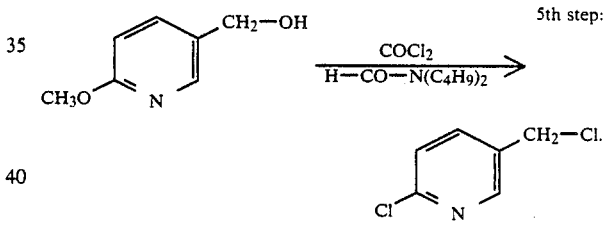

Suitable diluents for carrying out step one of the process according to the invention are inert organic solvents. Benzene, toluene, xylene, chlorobenzene, dichlorobenzene, nitrobenzene or phosphorus oxychloride are particularly preferably used. It is also possible to carry out step one of the process according to the invention directly in substance, without using a diluent.

When carrying out step one of the process according to the invention, the reaction temperatures can be varied within a substantial range. In general, the process is carried out at temperatures between 80° C. and 180° C., preferably at temperatures between 110° C. and 160° C.

For carrying out step one of the process according to the invention, either 2 to 4 moles of phosphorus pentachloride or, in order to avoid a substantial excess of phosphorus pentachloride, initially 1 to 2 moles of thionyl chloride (in this process the starting substance nicotinic acid is converted into the hydrochloride of the corresponding acid chloride) and then 1 to 2 moles of phosphorus pentachloride are employed per mole of nicotinic acid, of the formula (II). It is also possible to prepare phosphorus pentachloride directly in the reaction vessel, from an appropriate amount of phosphorus trichloride and an equivalent amount of chlorine. In the course of the reaction, it is expedient to continuously distil off phosphorus oxychloride which has been evolved.

The reaction product of the formula (III) can be isolated by distillation; but it is also possible to employ the crude product for the further reaction.

Formula (IV) provides a general definition of the alkali metal alkoxides required as starting substances for carrying out step two of the process according to the invention. In this formula (IV), R preferably represents a straight-chain or branched alkyl having 1 to 4 carbon atoms, in particular represents methyl, ethyl, isopropyl, i-butyl or sec-butyl.

M preferably represents a sodium or potassium cation, in particular represents a sodium cation.

The alkali metal alkoxides of the formula (IV) are generally known compounds; if required, they can be prepared in situ from alkali metal hydroxides and corresponding alkoxides.

Suitable diluents for carrying out step two of the process according to the invention are also inert organic solvents. Lower alkyl alcohols, which carry the same alkyl radical by which the alkali metal alkoxides of the formula (IV) to be used as reactants are characterized, in particular methanol, ethanol, isopropanol or isobutanol, are particularly preferably used.

When carrying out step two of the process according to the invention, the reaction temperatures can be varied within a substantial range. In general, the process is carried out at temperatures between 0° C. and 120° C., preferably at temperatures between 20° C. and 90° C.

For carrying out step two of the process according to the invention, 3.0 to 15.0 moles, preferably 3.0 to 6.0 moles, of alkali metal alkoxide of the formula (IV) are generally employed per mole of 3-trichloromethylpyridine of the formula (III). The reaction is carried out and the reaction products are worked up and isolated by known methods (cf. the Preparation Examples).

Suitable catalytic acids for carrying out step three of the process according to the invention are dilute inorganic or organic acids. Dilute aqueous hydrochloric acid, sulphuric acid, formic acid or acetic acid is preferably used as the reaction medium. It is also possible to carry out the reaction in pure water as the reaction medium, without employing a catalyst acid.

When carrying out step three of the process according to the invention, the reaction temperatures can be varied within a substantial range. In general, the process is carried out at temperatures between 0° C. and 100° C., preferably at temperatures between 20° C. and 80° C.

For carrying out step three of the process according to the invention, 10.0 to 50.0 moles of water and, if appropriate, 0.01 to 10.0 moles of catalyst acid are generally employed per mole of pyridine ether acetal of the formula (V). The reaction is carried out and the reaction products are worked up and isolated by generally customary methods (cf. also the Preparation Examples).

Suitable hydrogenation catalysts for carrying out step four of the process according to the invention are customary noble metal catalysts, noble metal oxide catalysts or Raney catalysts, if appropriate on a suitable support, such as, for example, active carbon, alumina or silicon dioxide. Palladium on active carbon or Raney nickel are particularly advantageously used.

Suitable diluents for carrying out step four of the process according to the invention are inert organic solvents. These in particular include ethers, such as diethyl ether, dioxane, tetrahydrofuran or ethyl glycol dimethyl ether or ethyl glycol diethyl ether, alcohols, such as methanol, ethanol, propanol, butanol, ethylene glycol monomethyl ether or ethylene glycol monoethyl ether, or acids, such as, for example, acetic acid.

When carrying out step four of the process according to the invention, the reaction temperatures can be varied within a substantial range. In general, the process is carried out at temperatures between 0° C. and 150° C., preferably at temperatures between 20° C. and 100° C.

Step four of the process according to the invention is carried out either under atmospheric pressure or under increased or reduced pressure. In general, the process is carried out in pressure ranges between 0.01 and 200 bar, preferably between 0.1 and 100 bar.

For carrying out step four of the process according to the invention, 1.0 to 20.0 moles, preferably 1.0 to 5.0 moles, of hydrogen and 0.0001 to 1.0 mole, preferably 0.01 to 0.1 mole, of hydrogenation catalyst are generally employed per mole of pyridine aldehyde of the formula (VI). The reaction is carried out and the reaction products are worked up and isolated by generally customary methods (cf. also the Preparation Examples).

Suitable chlorinating agents for carrying out step five of the process according to the invention are, in particular, phosphorus pentachloride, phosphorus oxychloride or phosgene, as well as mixtures of these compounds.

Step five of the process according to the invention can be carried out either directly in substance without the addition of a diluent, or in the presence of a suitable diluent. These in particular include aliphatic, alicyclic or aromatic, optionally halogenated hydrocarbons, such as, for example, benzene, toluene, xylene, chlorobenzene or dichlorobenzene, petroleum ether, hexane, cyclohexane, dichloromethane, chloroform or carbon tetrachloride.

If appropriate, step five of the process according to the invention can be carried out in the presence of a suitable reaction auxiliary. Suitable reaction auxiliaries are tertiary amines, such as triethylamine, N,N-dimethylaniline, pyridine or N,N-dimethylaminopyridine, and in addition catalytic amounts of formamides, such as, for example, N,N-dimethylformamide or N,N-dibutylformamide, or inorganic metal chlorides, such as magnesium chloride or lithium chloride.

When carrying out step five of the process according to the invention, the reaction temperatures can be varied within a substantial range. In general, the process is carried out at temperatures between 20° C. and 200° C., preferably at temperatures between 60° C. and 150° C.

For carrying out step five of the process according to the invention, 1.0 to 10.0 moles, preferably 1.0 to 5.0 moles, of chlorinating agent and, if appropriate, 0.01 to 3.0 moles, preferably 0.1 to 2.0 moles, of reaction auxiliary are generally employed per mole of pyridylmethanol of the formula (VII).

In particular when gaseous chlorinating agents are used, the course of the reaction may be monitored with the aid of checking by thin-layer chromatography. The reaction products are worked up by customary methods.

When the "one-pot variants" are carried out, the procedure is followed in which water and if necessary an appropriate amount of catalyst acid are added at room temperature to the reaction mixture which is obtained in step 2 of the process according to the invention and which is present as a solution in methanol*, then stirring the mixture for 0.5 to 20 hours at the temperature required**, and a hydrogenation catalyst and, if required, an additional solvent is added to the reaction mixture, the mixture is hydrogenated in a customary manner at the temperature required and the pressure required, and the mixture is rendered neutral when the hydrogenation is complete, insoluble constituents are filtered off and the filtrate is worked up by means of distillation (cf. also the Preparation Examples).

* At this point it is also possible to employ isolated and purified product from step 2 of the process according to the invention.
** At this point it is also possible to work up the mixture as described in the case of step 2 according to the invention and to carry out the subsequent hydrogenation in a separate reaction.

The compound 2-chloro-5-chloromethylpyridine, of the formula (I), is a known compound, and it can be obtained with the aid of the process according to the invention and used, for example, as an intermediate for the preparation of insecticidal nitromethylene compounds (cf., for example, EP-A 163,855; EP-A 192,060; EP-A 259,738; EP-A 254,859).

PREPARATION EXAMPLES

Step 1:

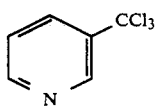

123.1 g (1 mol) of nicotinic acid are added in the course of 10 minutes to 250 ml of thionyl chloride, during which process the temperature of the mixture rises to 50° C. When the addition is complete, the mixture is stirred at 55° C. for 15 minutes, and excess thionyl chloride is then distilled off under reduced pressure. 275 g (2 mol) of phosphorus trichloride are then added, and a total of 140 g (2 mol) of dried chlorine gas is passed in the course of 2 hours, during which process the temperature of the mixture rises to 70° C. After this, the mixture is heated for one hour at 150° C., during which process any phosphorus oxychloride which is evolved is continuously distilled off. For working up, the mixture is cooled, 600 ml of ethyl acetate are added, the mixture is poured into ice water and rendered weakly alkaline by adding sodium carbonate in portions and with cooling, the organic phase is separated off, and the aqueous phase is extracted using 300 ml of ethyl acetate. The combined organic phases are dried over magnesium sulphate, concentrated in vacuo and distilled under a waterpump vacuum.

176.8 g (89% of theory) or 3-trichloromethylpyridine of boiling point 105° C. to 107° C. at 15 mbar are obtained.

Step 2:

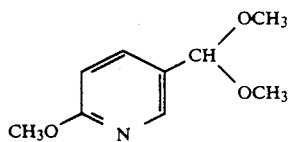

31.6 g (0.161 mol) of 3-trichloromethylpyridine are added dropwise and with stirring in the course of 45 minutes at reflux temperature to 140.7 g (0.515 mol) of a solution of sodium methoxide in methanol. When the addition is complete, the mixture is stirred for 3 more hours at reflux temperature and then cooled and filtered, the filtrate is concentrated, the residue is taken up in dichloromethane, the mixture is filtered once again, the filtrate is concentrated, and the residue is distilled in vacuo.

24.5 g (83% of theory) of 2-methoxy-5-bis(methoxy)-methyl-pyridine of boiling point 54° C. to 55° C. at 0.25 mbar are obtained.

Step 3:

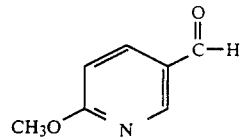

20 ml of concentrated aqueous hydrochloric acid are added to 20 g (0.109 mol) of 2-methoxy-5-bis-(methoxy)methylpyridine in 100 ml of water, the mixture is stirred for 1 hour at room temperature and then cooled to 0° C., and the solid which has precipitated is filtered off with suction.

12.9 g (82% of theory) of 6-methoxypyridine-3-aldehyde of melting point 47° C. to 49° C. are obtained.

Step 4:

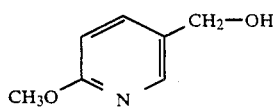

2 g of Raney nickel are added to 10.9 g (0.08 mol) of 6-methoxypyridine-3-aldehyde in 100 ml of ethanol, and the mixture is subsequently hydrogenated at 75° C. and 50 bar hydrogen pressure for 3 hours. For working up, the catalyst is filtered off and the filtrate is concentrated in vacuo.

11.1 g (100% of theory) of 2-methoxy-5-hydroxymethylpyridine are obtained as an oil which can be purified by distillation, of boiling point 85° C. to 88° C. at 0.6 mbar.

Step 5:

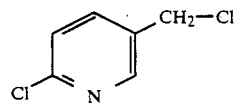

6.5 g (0.041 mol) of N,N-dibutylformamide are added to 28.6 g (0.206 mol) of 2-methoxy-5-hydroxymethylpyridine in 100 ml of toluene, the mixture is heated to 80° C., and a stream of phosgene is slowly passed into the solution until the starting material is no longer detectable in the thin-layer chromatogram (silica gel; eluent petroleum ether/ethyl acetate 5:1; about 2.5 hours). For working up, excess phosgene is removed by expelling at 80° C. using nitrogen, the mixture is then cooled to room temperature, water is added, a slightly alkaline pH is established by adding sodium carbonate, the organic phase is separated off, the aqueous phase is extracted using 50 ml of toluene, the combined organic phases are dried over magnesium sulphate, and the solvent is removed under reduced pressure.

High-vacuum distillation gives 27.6 g (88% of theory) of 2-chloro-5-chloromethylpyridine of boiling point 70° C. to 80° C. at 1 mn.

Step 2+step 3+step 4:

(One-pot version)

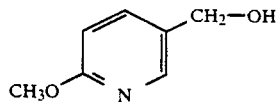

98.3 g (0.5 mol) of 3-trichloromethylpyridine are added dropwise and with stirring, in the course of 25 minutes at reflux temperature to 344 g (1.6 mol) of a solution of sodium methoxide in methanol; when the addition is complete, the mixture is heated at the boiling point for 5 more hours and then cooled to room temperature, 100 ml of water are added, and a pH of 3 to 4 is established by adding 15 ml of concentrated aqueous hydrochloric acid. The mixture is stirred at room temperature for 14 hours, 10 g of palladium on active carbon (10% of Pd) are then added, 40 ml of water are added, and the mixture is hydrogenated under atmospheric pressure and with vigorous stirring. After 3.5 hours (hydrogen uptake: 10.790 l), the mixture is rendered neutral using saturated aqueous sodium hydrogen carbonate solution and filtered, the filtrate is concentrated, the residue is taken up in ethyl acetate, and the mixture is filtered again, concentrated and distilled.

52.5 g (76.6% of theory) of 2-methoxy-5-hydroxymethylpyridine of boiling point 85° C. to 88° C. at 0.6 mbar are obtained.

Step 2+step 3:

(One-pot version)

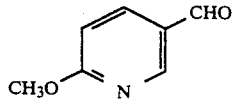

50 g (0.254 mol) of 3-trichloromethyl-pyridine are added dropwise in the course of 15 minutes at reflux temperature to a mixture of 32.6 g (0.815 mol) of sodium hydroxide and 200 ml of methanol. The reaction mixture is refluxed for 60 more minutes and cooled to 20° C., and first 100 ml of water and then 25 ml of concentrated hydrochloric acid are then added. After the mixture had been stirred for 3 hours at 20° C., it is concentrated to about 100 ml, again diluted with water, and extracted twice using ethyl acetate. The combined extraction solutions are dried using sodium sulphate and filtered. The solvent is carefully removed from the filtrate by distillation under a waterpump vacuum.

27.2 g (78.5% of theory) of 6-methoxypyridine-3-aldehyde of melting point 47° C. to 49° C. are obtained.

It will be appreciated that the instant specification and claims are set forth by way of illustration and not limitation, and that various modifications and changes may be made without departing from the spirit and scope of the present invention.

What is claimed is:

1. A process for the preparation of 2-chloro-5-chloromethylpyridine, of the formula (I),

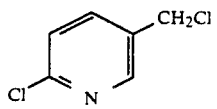

comprising (a) reacting in a first step nicotinic acid of the formula (II)

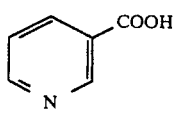

with phosphorus pentachloride, (b) reacting in a second step the resulting 3-trichloromethylpyridine from the first step, of the formula (III),

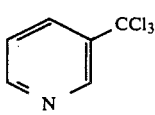

with an alkali metal alkoxide of the formula (IV)

 (IV)

in which
R represents alkyl and
M represents an alkali metal cation,
(c) reacting in a third step the resulting pyridine ether acetal from the second step, of the formula (V)

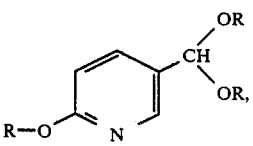

in which R has the abovementioned meaning, with water, (d) hydrogenating in a fourth step the resulting pyridine aldehyde from the third step, of the formula (VI)

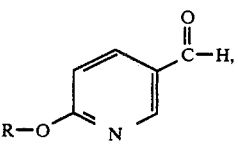

p0 in which R has the abovementioned meaning, with molecular hydrogen in the presence of a hydrogenation catalyst, and finally (e) reacting in a fifth step the resulting pyridylmethanol from the fourth step, of the formula (VII)

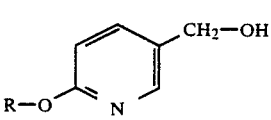

in which R has the abovementioned meaning, with a chlorinating agent in the presence of a diluent.

2. A process according to claim 1, wherein either step two and step three, or step three and step four, or steps two, three and four, are carried out directly in one reacting step without isolation of the intermediates.

3. A process according to claim 1, wherein steps two and three are carried out without isolation of the intermediates.

4. A process according to claim 1, wherein steps three and four are carried out without isolation of the intermediates.

5. A process according to claim 1, wherein steps two, three and four are carried out without isolation of the intermediates.

6. A process according to claim 1, wherein in the first step the nicotinic acid and phosphorous pentachloride are reacted in the presence of thionyl chloride.

7. A process according to claim 1, wherein int he first step the nicotinic acid and phosphorous pentachloride are reacted in the presence of a diluent.

8. A process according to claim 1, wherein in the second step the 3-trichloromethylpyridine and alkali metal alkoxide are reacted in the presence of a diluent.

9. A process according to claim 1, wherein in the third step the pyridine ether acetal and water are reacted in the presence of a catalyst acid.

10. A process according to claim 1, wherein in the fourth step the pyridine aldehyde is hydrogenated in the presence of a diluent.

11. A process according to claim 1, wherein in the fifth step the pyridylmethanol and the chlorinating agent are reacted in the presence of a reaction auxiliary.

12. A process according to claim 11, wherein the reaction auxiliary is selected from the group consisting of tertiary amines, formamides and inorganic metal chlorides.

13. A process according to claim 1, wherein R is a straight-chain or branched alkyl having 1 to 4 carbon atoms.

* * * * *